United States Patent [19]
Schroeder et al.

[11] 3,996,252
[45] Dec. 7, 1976

[54] PREPARATION OF PURE 1,8-DINITROANTHRAQUINONE

[75] Inventors: Bernd Schroeder, Odenthal; Wolfgang Auge; Karl-Werner Thiem, both of Cologne; Rütger Neeff, Leverkusen, all of Germany

[73] Assignee: Bayer Aktiengesellschaft, Leverkusen, Germany

[22] Filed: Apr. 1, 1976

[21] Appl. No.: 672,690

[30] Foreign Application Priority Data

Apr. 19, 1975 Germany ........................ 2517435

[52] U.S. Cl. .............................................. 260/369
[51] Int. Cl.$^2$ .................... C07C 79/37; C09B 1/00
[58] Field of Search ................................... 260/369

[56] References Cited
UNITED STATES PATENTS 3,786,073    1/1974    Frey et al. ........................ 260/369

*Primary Examiner*—Paul F. Shaver
*Attorney, Agent, or Firm*—Burgess, Dinklage & Sprung

[57] ABSTRACT

A mixture of dinitroanthraquinones of which at least 70% is 1,8-dinitroanthraquinone is dissolved at elevated temperature in a halogenated aromatic hydrocarbon, a carboxylic acid nitrile or a cyclic sulphone and is thereafter cooled selectively to precipitate substantially pure 1,8-dinitroanthraquinone. Preferred solvents are 1-chloronaphthalene, sulpholane and adipic acid dinitrile. The particular temperature of dissolution and cooling will depend upon the particular solvent.

11 Claims, No Drawings

PREPARATION OF PURE 1,8-DINITROANTHRAQUINONE

The present invention relates to a process for the preparation of pure 1,8-dinitroanthraquinone.

The complete nitration of anthraquinone to dinitroanthraquinones in sulphuric acid with nitric acid (Hefti; Helv. 14, page 1404 (1939)) and in pure nitric acid (Boettger and Petersen, Ann. 166, page 154 (1881)) gives mixtures of dinitroanthraquinones which essentially consist of 1,5-, 1,8-, 1,6- and 1,7-dinitroanthraquinones. 1,5- and 1,8-dinitroanthraquinones are important intermediate products for the preparation of dyestuffs (see Colour Index 65,405, 65,415, 69,015 and 70,510). A prerequisite for this is, however, that these substances must be as free as possible from 1,6- and 1,7-dinitroanthraquinones.

There has therefore been no lack of attempts to isolate 1,5-dinitroanthraquinone and 1,8-dinitroanthraquinone which are as pure as possible from the mixtures of dinitroanthraquinones obtained from the nitration of anthraquinone.

For these purposes, the dinitroanthraquinones were, for example, precipitated from the corresponding reaction medium by adding water, dried and recrystallized from organic solvents, such as alcohol, glacial acetic acid, acetone or nitrobenzene (German Patent Specifications 167,699 and 72,685, Hefti, Helv. 14, page 1404 (1931) and Römer, Ber. 16, page 365).

It is further known from U.S. Pat. No. 2,309,708 to isolate 1,5-dinitroanthraquinone and 1,8-dinitroanthraquinone from mixtures of dinitroanthraquinones by heating these mixtures with aqueous sodium sulphite solution for 2–4 hours. However, separation of the mixture of 1,5-dinitroanthraquinone and 1,8-dinitroanthraquinone thus obtained cannot be achieved in this way.

Polish Pat. No. 52,206 describes a process in which anthraquinone is nitrated in hydrofluoric acid and the dinitroanthraquinones formed are separated off and stirred thoroughly with concentrated nitric acid at 50° C. All the compounds except 1,5-dinitroanthraquinone go into solution. After separating off the 1,5-dinitroanthraquinone, 1,8-dinitroanthraquinone is precipitated out of the filtrate by adding glacial acetic acid, while 1,6-dinitroanthraquinone and 1,7-dinitroanthraquinone remain in solution.

The disadvantage of this process is that nitric acid/glacial acetic acid mixtures are not without danger and are difficult to handle industrially.

It is also known to separate 1,5-dinitroanthraquinone and 1,8-dinitroanthraquinone by treating mixtures of dinitroanthraquinones with certain aromatic hydrocarbons which contain nitro groups, for example nitrobenzene or nitrotoluene. However, in this way, 1,5-dinitroanthraquinone is obtained in a purity of only 93.5% German Published Specification DAS 2,248,704) or 95.3% (Japanese laid-open Patent Application No. 49.76851) and 1,8-dinitroanthraquinone is obtained in a purity of only 82.5%.

It has now been found that even purer 1,8-dinitroanthraquinone can be isolated in a technically advantageous manner from mixtures of dinitroanthraquinones which contain at least about 70% by weight of 1,8-dinitroanthraquinone when such mixtures are treated with a solvent at elevated temperature and cooled and the 1,8-dinitroanthraquinone which crystallizes out is separated off, and isolated, in a manner which is in itself known.

Mixtures of dinitroanthraquinones which contain at least 70% by weight of 1,8-dinitroanthraquinone can be obtained, for example, by nitrating anthraquinone and/or 1-nitroanthraquinone in a manner which is in itself known, for example with nitric acid alone or with a mixture of nitric acid and sulphuric acid, and subjecting the mixture thus obtained to partial or complete separation of 1,5-dinitroanthraquinone. The nitration of anthraquinone and/or 1-nitroanthraquinone is described, for example, in German Published Specification DOS 2,143,253 and German Published Specification DOS 2,306,611. The reaction conditions, such as the temperature, the molar ratio of nitric acid to anthraquinone, or the concentration of nitric acid, under which the nitration is carried out are not critical within the scope of the process according to the invention. 1,5-Dinitroanthraquinone can be separated off, for example, in a manner which is in itself known and is relatively simple, on the basis of its insolubility in concentrated nitric acid. Thus, for example, in the case of the direct nitration of anthraquinone with concentrated nitric acid, 1,5-dinitroanthraquinone is already obtained in the reaction mixture as an insoluble precipitate and thus can substantially be separated from the other dinitroanthraquinones by simple filtration. In an advantageous embodiment which forms the subject of our Copending Application Serial No. 677,688, filed Apr. 1, 1976, 1,5-dinitroanthraquinone can also be separated off by treating the mixture of dinitroanthraquinones, containing at least 35 % by weight of 1,5-dinitroanthraquinone, which is obtained from the nitration, at elevated temperature with a solvent to be used according to the invention, cooling the mixture, filtering off the 1,5-dinitroanthraquinone which precipitates. Crude 1,8-dinitroanthraquinone is then isolated from the filtrate thus obtained, either by distilling off the solvent or by precipitation with alcohols, such as methanol, ethanol or butanol. The crude 1,8-dinitroanthraquinone which is thus obtained and which is substantially freed from 1,5-dinitroanthraquinone, can then be subjected to the process according to the invention.

It has also been possible to make up starting mixtures which are suitable for the process according to the invention by mixing the reaction products from various nitrations of anthraquinone or from the stages of their working up. In general, mixtures which can be employed in the process according to the invention can also contain, in addition to 1,8-dinitroanthraquinone, 1,5-dinitroanthraquinone, 1,6-dinitroanthraquinone and 1,7-dinitroanthraquinone and, in some cases, also traces of 2-nitroanthraquinone, 1-nitroanthraquinone and anthraquinone. The mixtures used as starting materials are those which contain 1,8-dinitroanthraquinone in amounts of at least about 70% by weight and in general up to 95% by weight and it has proved advantageous to employ those mixtures which contain about 75–90% by weight of 1,8-dinitroanthraquinone. Advantageously the content of 1,6- and 1,7-dinitroanthraquinones together in these mixtures should not be more than about 5% by weight.

Preferred solvents which can be employed within the scope of the process according to the invention are aromatic hydrocarbon, for example with 6 to 10 C atoms, which are monosubstituted or polysubstituted by halogen. Examples which may be mentioned are:

o-dichlorobenzene, 1,2,3-trichlorobenzene, 1,2,4-trichlorobenzene and chloronaphthalenes, such as, for example, 1-chloronaphthalene.

Nitriles which are derived from aromatic or aliphatic monocarboxylic acids or dicarboxylic acids can also be used and in the case of aliphatic monocarboxylic acids or dicarboxylic acids possible acids are, for example, those with 3 to 8 C atoms, preferably those with 5 to 7 C atoms. Examples which may be mentioned are: benzonitrile, adipic acid dinitrile, malonic acid dinitrile, succinic acid dinitrile, glutaric acid dinitrile and pimelic acid dinitrile.

Further solvents which can be employed within the scope of the process according to the invention are cyclic sulphones, for example tetramethylenesulphone (sulpholane), pentamethylenesulphone, 2-methyl-tetramethylenesulphone and hexamethylenesulphone.

Solvents which are preferably employed are: sulpholane, 1-chloronaphthalene and adipic acid dinitrile.

In general, the process according to the invention is carried out by initially taking the particular solvent at elevated temperature and stirring in the mixture of dinitroanthraquinones which is to be separated. In general, the solvent is initially introduced in 4 to 7 times the amount by weight of the mixture of dinitroanthraquinone employed. Depending on the solvent employed, elevated temperature is understood as temperatures of about 150° C up to the boiling point of the particular solvent, temperatures of about 170°–210° C being preferred. After all of the mixture of dinitroanthraquinones has been introduced, the mixture is preferably left at elevated temperature, while stirring, for some time, generally 30–240 minutes. It is then cooled, cooling being to temperatures of about 0°–200° C, preferably to temperatures of about 20°–180° C, depending on the solvent employed. Cooling down to the crystallization temperature should not take longer than about 5 hours. The 1,8-dinitroanthraquinone which crystallizes out can be isolated in a manner which is in itself known, for example by simple filtration. If, for example, sulpholane is used as the solvent, the mixture of dinitroanthraquinones is advantageously stirred in at temperatures of 160°–200° C and the mixture is then cooled to 20°–60° C. If 1-chloronaphthalene is used, the mixture of dinitroanthraquinones can advantageously be introduced at a temperature of 200°–250° C and the mixture can then be cooled to temperatures of 160° to 190° C for crystallization. A 1,8-dinitroanthraquinone can thus be obtained in a purity of 98% by weight and above and its purity can be further increased by repeated treatment with the particular solvent according to the invention.

The process according to the invention can be carried out both under normal pressure and under elevated or reduced pressure. In general, however, the reaction will be carried out under normal pressure. In the following Examples percentages are percentages by weight.

EXAMPLE 1

40 g of a mixture containing 1,8-dinitroanthraquinone (analysis: 84.0% of 1,8-dinitroanthraquinone and 14.0% of 1,5-dinitroanthraquinone) and obtained according to the process of German Published Specification DOS 2,143,253 are stirred in 160 g of sulpholane for 1 hour at 180° C. The solid is then completely dissolved. The mixture is then cooled to 20° to 25° C in the course of 30 minutes. It is stirred for a further 30 minutes at this temperature and filtered through a sintered glass suction filter. The filter cake is pressed off well and washed with 20 g of sulpholane and then with methanol until free from sulpholane. After recrystallizing twice, 22.1 g of 1,8-dinitroanthraquinone are obtained (98.5% by weight, yield: 64.7% of theory).

EXAMPLE 2

40 g of the mixture containing 1,8-dinitroanthraquinone, which was used in Example 1, are introduced into 280 g of 1-chloronaphthalene and the mixture is stirred for 2 hours at 210° C. It is allowed to cool to 180° C and stirred for a further 30 minutes. Using a sintered glass suction filter which can be heated to 180° C, the solid is filtered off and is then pressed off well. It is washed with 20 g of hot 1-chloronaphthalene at 180° C and then, after cooling, with methanol. This gives 16.7 g of 1,8-dinitroanthraquinone (98.6% by weight, yield: 49.0% of theory).

EXAMPLE 3

208 g of anthraquinone are stirred with 2,540 g of 99% strength nitric acid (molar ratio of nitric acid to anthraquinone, 40:1) for 1.75 hours at 35° C. About 165 g of water are then added, the 1,5-dinitroanthraquinone (a) which has precipitated is filtered off, the filtrate is diluted with a further 244 g of water and the 1,8-dinitroanthraquinone (b) which has precipitated is filtered off.
a. Yield: 111 g (36% of theory), 82.3% of 1,5-dinitroanthraquinone and 15.0% of 1,8-dinitroanthraquinone
b. Yield: 105 g (35% of theory), 19.2% of 1,5-dinitroanthraquinone and 79% of 1,8-dinitroanthraquinone 50 g of fraction (b) are stirred in 350 g of sulpholane at 190° C until all of the solid has gone into solution. The mixture is allowed to cool to 40° C in the course of 30 minutes, stirred for a further 30 minutes and filtered. After pressing off the filter cake, the latter is washed with 25 g of sulpholane and then with methanol. Recrystallizing twice gives 22.4 g of a 99.0% pure 1,8-dinitroanthraquinone (yield 56.2% of theory).

EXAMPLE 4

50 g of fraction (b) in Example 3 are stirred in 350 g of 1-chloronaphthalene for 2 hours at 210° C. After cooling to 180° C (a period of 30 minutes), the mixture is stirred for a further 30 minutes and filtered through a sintered glass suction filter heated to 180° C. The filter cake, which is pressed off well, is washed with 25 g of hot 1-chloronaphthalene at 180° C and, after cooling, with methanol until free from chloronaphthalene. 18.0 g of 98.6% pure 1,8-dinitroanthraquinone are obtained (yield: 45.0% of theory).

EXAMPLE 5

1,000 g of a nitration mixture consisting of 25.6% of 1-nitroanthraquinone, 40% of 2-nitroanthraquinone, 11.2% of anthraquinone, 10.5% of 1,8-dinitroanthraquinone, 1.9% of 1,5-dinitroanthraquinone and 10.7% of 1,6-/1,7-dinitroanthraquinone are stirred with 4,050 g of 99% strength nitric acid (molar ratio of nitric acid to nitratable products, 19:1) for 2.5 hours at 65° C. The mixture is then cooled to 0° C and the 1,5-dinitroanthraquinone (a) which has precipitated is filtered off. The filtrate is then diluted with 410 g of water (mole fraction 0.66) and the product (b) which has precipitated is separated off.

a. Yield: 374 g, 79.1% of 1,5-dinitroanthraquinone and 18% of 1,8-dinitroanthraquinone
b. Yield: 165 g, 5.4% of 1,5-dinitroanthraquinone and 92.0% of 1,8-dinitroanthraquinone.

50 g of product (b) are treated with 200 g of sulpholane analogously to Example 1. 32.2 g of a 99.0% pure 1,8-dinitroanthraquinone are already obtained after crystallizing twice. (Yield: 70% of theory).

EXAMPLE 6

50 g of fraction (b) in Example 5 are treated with 250 g of 1-chloronaphthalene, as described in Example 2. This gives 24.6 g of 1,8-dinitroanthraquinone (98.1% pure, yield: 53% of theory).

EXAMPLE 7

50 g of a mixture of dinitroanthraquinones, which contains 51.1% of 1,5-dinitroanthraquinone and 48.6% of 1,8-dinitroanthraquinone, are stirred in 200 g of sulpholane for 3 hours at 170° C. The mixture is allowed to cool to 140° C in the course of 30 minutes and is stirred for a further 1.5 hours at this temperature and then filtered through a sintered glass suction filter preheated to 140° C. The residue on the filter contains the 1,5-dinitroanthraquinone fraction. 24.1 g of a 1,8-dinitroanthraquinone fraction are isolated from the filtrate, either by distillation of the sulpholane under vacuum or by dilution with 200 g of methanol, and this fraction can be further purified by crystallizing twice, as described in Example 1. 12.5 g of 98.2% pure 1,8-dinitroanthraquinone are then obtained (yield: 50.7% of theory).

EXAMPLE 8

30 g of a mixture of dinitroanthraquinones (51.1% of 1,5-dinitroanthraquinone and 48.6% of 1,8-dinitroanthraquinone) are stirred in 180 g of 1-chloronaphthalene for 1 hour at 210° C. The mixture is allowed to cool to 180° C in the course of 30 minutes and is filtered at this temperature through a pre-heated sintered glass suction filter and the material on the filter is washed with 30 g of hot 1-chloronaphthalene. The residue on the filter contains the bulk of the 1,5-dinitroanthraquinone. 16.8 g of a 1,8-dinitroanthraquinone fraction are precipitated from the filtrate by adding methanol. If this fraction is treated as described in Example 2, 6.2 g of a 98% pure 1,8-dinitroanthraquinone are obtained (yield: 42% of theory).

It will be appreciated that the instant specification and examples are set forth by way of illustration and not limitation, and that various modifications and changes may be made without departing from the spirit and scope of the present invention.

What is claimed is:

1. A process for separating off 1,8-dinitroanthraquinone from a mixture of dinitroanthraquinones containing at least about 70% by weight of 1,8-dinitroanthraquinone, comprising dissolving such mixture in a solvent selected from the group consisting of a halogenated aromatic hydrocarbon, a nitrile of an aromatic or aliphatic carboxylic acid and a cyclic sulphone, and cooling said solution thereby selectively to precipitate substantially pure 1,8-dinitroanthraquinone.

2. The process according to claim 1, wherein said solvent is a chlorobenzene or chloronaphthalene.

3. The process according to claim 2, wherein said solvent is 1-choronaphthalene and dissolution is effected at a temperature of about 200° to 250° C.

4. The process according to claim 3, wherein the 1-chloronaphthalene containing dissolved 1,8-dinitroanthraquinone is cooled to about 160° to 190° C.

5. The process according to claim 1, wherein said solvent is the nitrile of an aliphatic or aromatic mono- or dicarboxylic acid having from 3 to 8 carbon atoms.

6. The process according to claim 5, wherein said solvent is adipic acid dinitrile and dissolution is effected at a temperature between about 150° C and the boiling point.

7. The process according to claim 1, wherein said solvent is an optionally methyl-substituted tetra-, penta- or hexa-methylene sulphone.

8. The process according to claim 7, wherein said solvent is sulpholane and dissolution is effected at a temperature between about 150° C and the boiling point.

9. The process according to claim 8, wherein the sulpholane containing dissolved 1,8-dinitroanthraquinone is cooled to about 0° to 200° C.

10. The process according to claim 1, wherein the mixture contains less than about 20% by weight of 1,5-dinitroanthraquinone.

11. The process according to claim 10, wherein the mixture contains about 75 to 90% by weight of 1,8-dinitroanthraquinone.

* * * * *